United States Patent [19]

Goel et al.

[11] Patent Number: 4,798,872

[45] Date of Patent: Jan. 17, 1989

[54] ALKYLENE PHOSPHONATE ACID ESTER POLYOLS

[75] Inventors: Anil B. Goel; Biau-Hung Chang, both of Worthington, Ohio

[73] Assignee: Ashland Oil, Inc., Ashland, Ky.

[21] Appl. No.: 856,550

[22] Filed: Apr. 28, 1986

[51] Int. Cl.$^4$ .......................... C07F 9/40; C08G 18/00
[52] U.S. Cl. ...................................... 558/186; 521/169
[58] Field of Search ................................ 558/105, 186

[56] References Cited

U.S. PATENT DOCUMENTS 3,970,729  7/1976  Walsh et al. ........................ 558/105

FOREIGN PATENT DOCUMENTS 954792  4/1964  United Kingdom ................ 558/105

*Primary Examiner*—Anton H. Sutto
*Attorney, Agent, or Firm*—John F. Jones

[57] ABSTRACT

A process for preparing hydroxy phosphonic acid ester polyols by reacting an alkenyl phosphonic acid with an alkylene oxide and the reaction of the resulting hydroxy phosphonic acid ester polyols with polyisocyanates to form polyurethanes is described.

2 Claims, No Drawings

ALKYLENE PHOSPHONATE ACID ESTER POLYOLS

This invention relates to a process for preparing novel, flame retardant polyurethanes by using hydroxy alkenyl phosphonic acid ester polyols as fire retarding additives in the reaction of polyols with polyisocyanates to form thermosetting polyurethanes. The alkenyl phosphonic acid ester polyols are obtained from the reaction of an alkenyl phosphonic acid, such as isopropenyl phosphonic acid with an alkylene oxide, such as propylene oxide. The hydroxyalkenyl phosphonic acid ester polyols are also good compatibilizing agents for conventional polyol mixtures and fluorocarbon blowing agents used in the production of polyurethane foams.

Although various phosphorus containing organic molecules have been used as fire retarding additives in various polymeric materials, the phosphorous containing polyols embodied in this invention have not been previously disclosed as flame retardant materials for use in the manufacture of thermosetting polyurethanes.

We have discovered that polyols obtained from the reaction of alkylene oxides, such as propylene oxide, with an alkenyl phosphonic acid, such as isopropenyl phosphonic acid, can be utilized along with other conventional polyols as fire retardants in the synthesis of polyurethanes and they can also be used as compatibilizing agents for fluorocarbon blowing agents in the formation of polyurethane foams.

The following equation illustrates the formation of the flame retardant polyols of this invention.

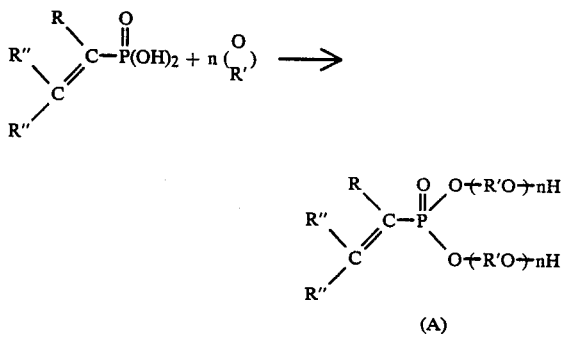

(A)

wherein n represents a number of from 1 to 50 in the polyol (A) and R is an alkyl group having from 1 to 10 carbon atoms or a phenyl group, R' is an alkylene group having from 2 to 4 carbon atoms and R" independently represents hydrogen or an alkyl group having from 1 to 10 carbon atoms.

A typical polyol of the type (A) is obtained from the reaction of isopropenyl phosphonic acid with propylene oxide and the resulting polyol has been found to be compatible with short- and long-chain polyols and the mixtures of these polyols, upon reaction with polyisocyanates, result in polyurethane polymer formation. The resulting polyurethane polymers have been found to have a higher degree of fire resistance compared to the polyurethane polymers obtained without the use of the alkenyl phosphonic acid ester polyols of this invention.

The alkylene oxides useful in the preparation of the alkenyl phosphonic acid ester polyols include ethylene oxide, propylene oxide, tetramethylene oxide, styrene oxide, the glycidyl ether of phenolics such as Bisphenol-A, cyclohexene oxide, vinyl cyclohexene dioxide, and the like. Most preferred are ethylene oxide propylene oxide, and tetramethylene oxide.

Alkenyl phosphonic acids which are useful in the preparation of the flame retardant polyols embodied in this invention include isopropenyl phosphonic acids, vinyl phosphonic acid, phenethylene phosphonic acid and the like. Most preferred is isopropenyl phosphonic acid because of its ready availability.

Polyols, in addition to the flame retardant polyols of this invention, which can be used in the formation of flame retardant polyurethanes include those having at least two hydroxyl groups per molecule and having equivalent weights falling in the range of from 20 to 5000. Specific polyols include butane diol, cyclohexane dimethanol, tripropylene glycol, amide diols, urethane diols, polyether polyols such as poly (tetramethylene ether) diols, poly (propylene ether) polyols, polyester polyols, and the like.

Polyhydroxy polyethers are suitable polyols and preferably those having at least 2 hydroxyl groups per molecule. Polyhydroxy polyethers can be prepared by polymerization of epoxides such as ethylene oxide, propylene oxide, butylene oxide, tetrahydrofuran, styrene oxide, or epichlorohydrin either on their own or by chemical addition to other materials such as ethylene glycol, propylene glycol, trimethylol propanes and 4,4'-dihydroxy diphenyl propane. Sucrose polyethers also may be used. Polybutadienes having hydroxyl groups as well as other known hydroxyl containing vinyl addition polymerized polymers can be used.

According to the present invention, hydroxyl containing polyesters, polythioethers, polyacetals, polycarbonates or polyesteramides of the types known for the formation of polyurethanes may also be used.

The polyisocyanates useful in this invention include organic isocyanates having at least two isocyanate groups per molecule. The polyisocyanates can be of low, high or intermediate molecular weight and can be any of a wide variety of organic polyisocyanates including ethylene diisocyanate, trimethylene diisocyanate, dodecamethylene diisocyanate, hexamethylene diisocyanate, hexamethylene diisocyanate trimer, tetraethylene diisocyanate, pentamethylene diisocyanate, propylene-1,2-diisocyanate, 2,3-dimethyl tetramethylene diisocyanate, butylene-1,2-diisocyanate, butylene-1,3-diisocyanate, 1,4-diisocyanato cyclohexane, cyclopentene-1,2-diisocyanate, p-phenylene diisocyanate, 1-methyl phenylene-1,2-diisocyanate, naphthalene-1,4-diisocyanate, toluene diisocyanate, diphenyl-4,4'-diisocyanate, benzene-1,2,4-triisocyanate, xylene-1,4-diisocyanate, xylylene-1,3-diisocyanate, 4,4'-diphenylene methane diisocyanate, 4,4'-diphenylene propane diisocyanate, 1,2,3,4-tetraisocyanato butane, butane-1,2,3-triisocyanate, polymethylene polyphenyl isocyanate, and other polyisocyanates having an isocyanate functionality of at least two more fully disclosed in U.S. Pat. Nos. 3,350,362 and 3,382,215. Polyisocyanates which are polymeric in nature including isocyanate prepolymers of all types are included in this invention.

In the preparation of the polyurethanes of this invention the hydroxyl equivalent to isocyanate equivalent ratios can be in the range of 0.85:1 to 1:10, respectively. When more than one isocyanate equivalent per hydroxyl equivalent is used, thermosetting polyurethane polymers result.

In the formation of polyurethanes in accordance with this invention catalysts which are known to catalyze polyurethane formation can be used. Such catalysts include tertiary amines, organotin carboxylates, metal salts such as lithium chloride, zinc carboxylates, iron acetyl acetonate, tetraalkyl ammonium halides and the like. Furthermore, because the alkenyl phosphonic acid ester polyols contain vinyl carbon-to-carbon unsaturation, the vinyl function can be used for further copolymerization with other vinyl monomers such as styrene, acrylates, methacrylates, acrylonitrile, hydroxy alkyl acrylates or methacrylates, and the like.

It has further been found that the alkenyl phosphonic acid ester polyols of this invention act as excellent compatibilizing agents. Thus, small amounts of the polyols of formula (A) above compatibilize mixtures of polyterephthalic ester polyols obtained from the transesterification of dimethyl terephthalate with low molecular weight glycols and the fluorocarbon blowing agent used for the production of cellular polyurethane polymers. The polyterephathalic ester polyols are more fully described in U.S. Pat. No. 3,647,759. The lack of compatibility of these polyterephathalic ester polyols with fluorocarbon blowing agents is more fully described in U.S. Pat. No. 4,444,916.

Other additives such as plasticizers, fillers, pigments, reinforcing fibers, and the like which are known to those skilled in the art can be included in the cellular and non-cellular polyurethanes which can be produced within the scope of this invention.

This invention is further illustrated in the following representative examples.

EXAMPLE I

In a reactor equipped with a mechanical stirrer and a reflux condenser were placed 503 g of isopropenyl phosphonic acid and then 475.2 g of propylene oxide were added slowly under constant stirring. An exothermic reaction occurred. The reactor was cooled and the temperature was maintained near room temperature. A part (567 g) of the resulting viscous liquid was transferred to an autoclave and was charged with 303 g of propylene oxide. The resulting mixture was allowed to react at 100 degrees C. for approximately two hours. The resulting viscous liquid was degassed under reduced pressure on a rotary evaporator. The clear liquid product was analyzed and found to have a hydroxyl number of 253 and an acid value of 1. This isopropenyl phosphonic acid polyol was used in subsequent Examples.

EXAMPLE 2

This experiment shows the use of the isopropenyl phosphonic acid ester polyol of Example 1 as a compatibilizing agent. In a one-ounce jar were placed 10 g of a diethylene glycol blend of terephthalic ester polyol having a hydroxyl number of 477 (commercially available from Chardinol Corp. as Chardol 560) and 2 g of the polyol described in Example 1. The resulting homogeneous solution was mixed vigorously with 4 g of fluorocarbon blowing agent (Freon F11B from DuPont Co.-trichlorofluoromethane) to give a homogeneous solution. The closed jar was kept at room temperature undisturbed for two hours during which time no separation occurred. An additional 2.3 g of the Freon were added and the mixed homogeneous solution was kept at room temperature for another two hours during which time no phase separation occurred.

EXAMPLE 3

This is a comparative example outside the scope of this invention. The process of Example 2 was followed using 10.1 g of the diethylene glycol blend of terephthalic ester polyol and 4 g of the fluorocarbon blowing agent. The vigorously stirred mixture was kept in the closed jar at room temperature and phase separation was observed within five minutes of standing undisturbed.

EXAMPLE 4

The polyol of Example 1 (15 g) was mixed with 0.3 g of N,N',N-tris(dimethylamine propyl) hexahydrotriazine, 0.03 g of dibutyltin dilaurate, 0.4 g of silicone surfactant (Dow Corning DC-193) and 5 grams of fluorinated hydrocarbon blowing agent (Freon F11B). The resulting solution was mixed rapidly with 20 g of carbodiimide group containing liquid methylene bis(phenyl isocyanate) (NCO equivalent weight 144). Rapid reaction occurred to give a foam having the following formation characteristics: cream time of 30 seconds, rise time of 62 seconds and tack-free time of 80 seconds. This foam was postcured at 100 degrees C. for 10 minutes to give a product which was found to have a density of 2.3 pounds/cubic foot and was also found to be non-flammable.

EXAMPLE 5

The procedure of Example 4 was followed using 12 g of the terephthalic ester polyol of Example 2, 5 g of the polyol of Example 1, 0.35 g of the tertiary amine catalyst, 0.4 g of the silicone surfactant, 5 g of the fluorocarbon blowing agent and the mixture was treated with 26 g of the polyisocyanate. Foaming occurred rapidly giving a cream time of 20 seconds, a rise time of 38 seconds and a tack free time of 42 seconds. The final foam had a non-friable surface, a density of 1.95 pounds/cubic foot and the compressive strength was 18 psi. The foam was found to be self-extinguishing.

EXAMPLE 6

The procedure of Example 4 was followed using 12 g of the poly terephthalic ester polyol (hydroxyl number of 350, 4.0 g of the polyol of Example 1, 0.3 g of the tertiary amine catalyst, 0.02 g of t-butyl peroctoate, 0.4 g of silicone surfactant, 5 g of blowing agent and 25 g of polyisocyanate based on methylene bis-(phenyl isocyanate) (functionality of 2.3). The foam as it formed was found to have a cream time of 32 seconds, a rise time of 50 seconds and a tack free time of 60 seconds. The foam was postcured at 100 degrees C. for five minutes. No shrinkage was noticed and the surface was non-friable. The foam was self-extinguishing and had a density of 1.92 pounds/cubic foot and a compressive strength of 19 psi.

EXAMPLE 7

The procedure of Example 4 was followed using 11 g of polyterephathalic ester polyol (hydroxyl No. 447), 5 g of the polyol of Example 1, 0.35 g of the tertiary amine catalyst, 0.4 g of silicone surfactant, 7 g of talc filler, 5.4 g of fluorocarbon blowing agent and 25 g of the polyisocyanate. The foam had a cream time of 22 seconds, a rise time of 37 seconds and a tack free time of 43 seconds. The final polymer foam was found to be self-extinguishing to almost non-flammable. The final foam had a density of 2.3 pounds per cubic foot and a compressive strength of 19 psi.

EXAMPLE 8

A solution of 15 g of propylene glycol, 7 g of dipropylene glycol, 18 g of poly (propylene ether) triol (molecular weight of about 5500), 6 g of the polyol of example 1 and 0.4 g of the tertiary amine catalyst, was degassed on a rotary evaporator under reduced pressure. This solution was mixed rapidly with 105 g of degassed liquid methylene bis (phenyl isocyanate) and poured into a hot mold at 90 degrees C. The mold was prepared with two parallel glass plates which were coated with a silicone mold release agent and spaced apart by 1/8 inch spacers. Polymerization occurred within a minute at room temperature to give an opaque white polymer which was placed in an oven at 100 degrees C. for 30 minutes for post cure. The resulting polymer sheet showed a notched izod impact strength (ASTM D-256) of 1.0 foot pound/inch of notch and a heat distortion temperature (ASTM D-648) of 105 degrees C.

We claim:

1. An alkenyl phosphonic acid ester polyol composition having the formula

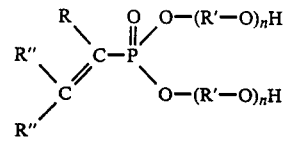

wherein n represents a number of from 1 to 50, R is an alkyl group having from 1 to 10 carbon atoms or a phenyl group, R' is an alkylene group having from 2 to 4 carbon atoms and R" independently represents hydrogen or an alkyl group having from 1 to 10 carbon atoms.

2. The polyol of claim 1 wherein R is methyl, R" is hydrogen and R' is propylene.

* * * * *